(12) United States Patent
Briner et al.

(10) Patent No.: US 6,638,936 B1
(45) Date of Patent: Oct. 28, 2003

(54) BENZOFURYLPIPERAZINE SEROTONIN AGONISTS

(75) Inventors: Karin Briner, Indianapolis, IN (US); Timothy Paul Burkholder, Carmel, IN (US); Mark Louis Heiman, Indianapolis, IN (US); David Lloyd Garver Nelson, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/031,310

(22) PCT Filed: Jul. 21, 2000

(86) PCT No.: PCT/US00/19545

§ 371 (c)(1),
(2), (4) Date: May 6, 2002

(87) PCT Pub. No.: WO01/09123

PCT Pub. Date: Feb. 8, 2001

Related U.S. Application Data

(60) Provisional application No. 60/172,169, filed on Dec. 17, 1999, and provisional application No. 60/146,287, filed on Jul. 29, 1999.

(51) Int. Cl.[7] ..................... A61K 31/496; C07D 405/10
(52) U.S. Cl. ................... 514/254.11; 544/376
(58) Field of Search ...................... 544/376; 514/254.11

(56) References Cited

U.S. PATENT DOCUMENTS 5,698,766 A    12/1997   Julius et al.

FOREIGN PATENT DOCUMENTS

| WO | EP 0 006 524 | 1/1980 |
| WO | EP 0 189 612 | 8/1986 |
| WO | WO 95 11243 | 4/1995 |
| WO | WO 97/08167 | 3/1997 |
| WO | WO 97/36893 | 10/1997 |

OTHER PUBLICATIONS

N[4]–Unsubstituted N[1]–Arylpiperazines as High–Affinity 5–HT1A Receptor Ligands, Wilma Kuipers;* Ineke van Wijngaarden;, Chris G. Kruse; Marian ter Horst–van Amstel; Martin Th. M. Tulp T and Adriaan P. Ijzerman, *J.MIHed. Chemn.* 1995, 38. 1942–1954.

*Primary Examiner*—Emily Bernhardt
(74) *Attorney, Agent, or Firm*—R. Craig Tucker

(57) ABSTRACT

The present invention provides serotonergic benzofurans of Formula I:

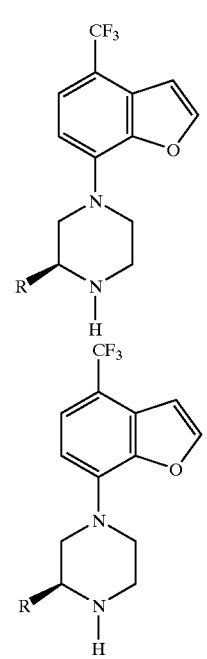

where R is methyl or ethyl, or pharmaceutically acceptable acid addition salts thereof.

18 Claims, No Drawings

BENZOFURYLPIPERAZINE SEROTONIN AGONISTS

This application claims priority to U.S. Provisional applications No. 60/146,287 filed Jul. 29, 1999 and No. 60/172,169, filed Dec. 17, 1999.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2a}$, 5-HT$_{2b}$, and 5-HT$_{2c}$. The 5-HT$_{2c}$ receptor has been isolated and characterized (Julius, et al., U.S. Pat. No. 4,985,352), and transgenic mice lacking the 5-HT$_{2c}$ receptor have been reported to exhibit seizures and an eating disorder resulting in increased consumption of food (Julius, et al., U.S. Pat. No. 5,698,766). Compounds selective for the 5-HT$_{2c}$ receptor would provide useful therapies for the treatment of seizure and eating disorders without the side effects associated with current therapies.

Hartog (Hartog, et al., U.S. Pat. No. 5,424,313) generically describes a number of benzofurylpiperazines which are taught to be useful as psychotropics, central analgetics, and thrombolytics. The use of benzofuryl-piperazines as selective 5-HT$_{2c}$ agonists has heretofore not been appreciated. The present invention provides compounds selective for the 5-HT$_{2c}$ receptor.

The present invention provides compounds of Formula I:

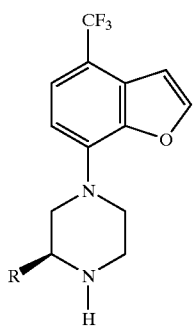

I where R is methyl or ethyl, or pharmaceutically acceptable acid addition salts thereof.

This invention also provides a pharmaceutical formulation which comprises, in association with a pharmaceutically acceptable carrier, diluent or excipient, a compound of Formula I.

The present invention provides a method for increasing activation of the 5-HT$_{2C}$ receptor in mammals comprising administering to a mammal in need of such activation a pharmaceutically effective amount of a compound of Formula I.

The present invention also provides a method for treating obesity in mammals comprising administering to a mammal in need of such treatment a pharmaceutically effective amount of a compound of Formula I.

A further embodiment of this invention is a method for increasing activation of the 5-HT$_{2C}$ receptor for treating a variety of disorders which have been linked to decreased neurotransmission of serotonin in mammals. Included among these disorders are obesity, obsessive compulsive disorder, and depression. Any of these methods employ a compound of Formula I.

This invention also provides the use of a compound of Formula I for the manufacture of a medicament for the treatment of obesity. Additionally, this invention provides a pharmaceutical formulation adapted for the treatment of obesity containing a compound of Formula I. Furthermore, this invention includes a method for the treatment of obesity which comprises administering an effective amount of a compound of Formula I.

DETAILED DESCRIPTION OF THE INVENTION

The compounds of Formula I are generally referred to as 1-(4-trifluoromethylbenzofur-7-yl)-3(S) -methylpiperazine when R is methyl, and 1-(4-trifluoromethylbenzofur-7-yl)-3(S)-ethylpiperazine when R is ethyl. Since this compound is an amine, it is basic in nature and accordingly reacts with any of a number of inorganic and organic acids to form pharmaceutically acceptable acid addition salts. It is preferable to convert the free amine to a pharmaceutically acceptable acid addition salt for ease of handling and administration. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid and fumaric acid.

The compounds of Formula I may be prepared by chiral chromatography of the racemic or enantiomerically enriched free amines, or fractional crystallization of salts prepared from racemic or enantiomerically enriched free amines and a chiral acid. Alternatively, the free amines may be reacted with a chiral auxiliary and the enantiomers separated by chromatography followed by removal of the chiral auxiliary to regenerate the free amines. Furthermore, separation of enantiomers may be performed at any convenient point in the synthesis of the compound of the invention. Preferably, the compounds of the invention are prepared beginning with chiral starting materials.

The present invention also provides a method for increasing activation of the 5-HT$_{2C}$ receptor in mammals by administering to a mammal in need of such activation a pharmaceutically effective amount of a compound of Formula I. The preferred mammal is human.

Compounds of Formula I may be prepared as described in the following scheme, beginning with 4-trifluorometh-yl-7-(substituted)-benzofuran and 2(S)-methyl- or ethylpiperazine.

Synthetic Scheme I

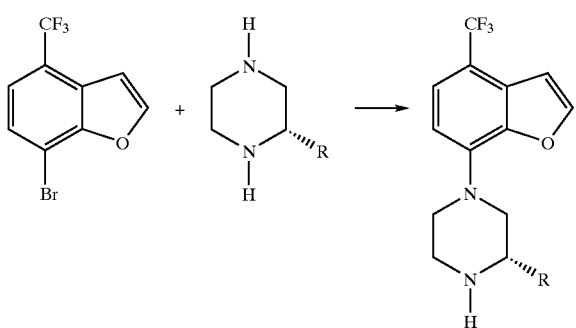

The 4-trifluoromethylbenzofur-7-yl bromide, iodide, or triflate is reacted with 2(S)-methyl- or ethylpiperazine in the presence of an appropriate catalyst and base. The coupling is catalyzed with an appropriate metal catalyst, such as nickel or palladium. Palladium catalysts are preferred and are either commercially available or may be generated in situ by combining trisdibenzylideneacetone dipalladium or palladium chloride with a phosphine ligand such as racemic 2,2'-bis(diphenylphosphino)-1,1'-binaphthyl, tri-o-tolylphosphine, or bis(diphenylphosphino)ferrocene. The ratio of palladium to phosphine ligand is typically between 1:1 and 1:5. Typically 0.01 to 0.1 equivalents of catalyst are used relative to starting benzofuran. Useful bases include sodium tert-butoxide, lithium tert-butoxide, and potassium tert-butoxide. Typically 1–5 equivalents of base are used relative to starting benzofuran.

The benzofuran, piperazine, catalyst, and base are combined in a suitable solvent. Suitable solvents include toluene, benzene, dioxane, and tetrahydrofuran. The mixture is stirred at 20–200° C. under an inert atmosphere, typically nitrogen or argon, until the reaction is complete. Additional portions of any reagent may be added during the course of the reaction as necessary or desired. Typically, 1–1.2 equivalents of the piperazine are reacted with the benzofuran.

Alternatively, the compounds of Formula I may be prepared as described in the following scheme.

Synthetic Scheme II

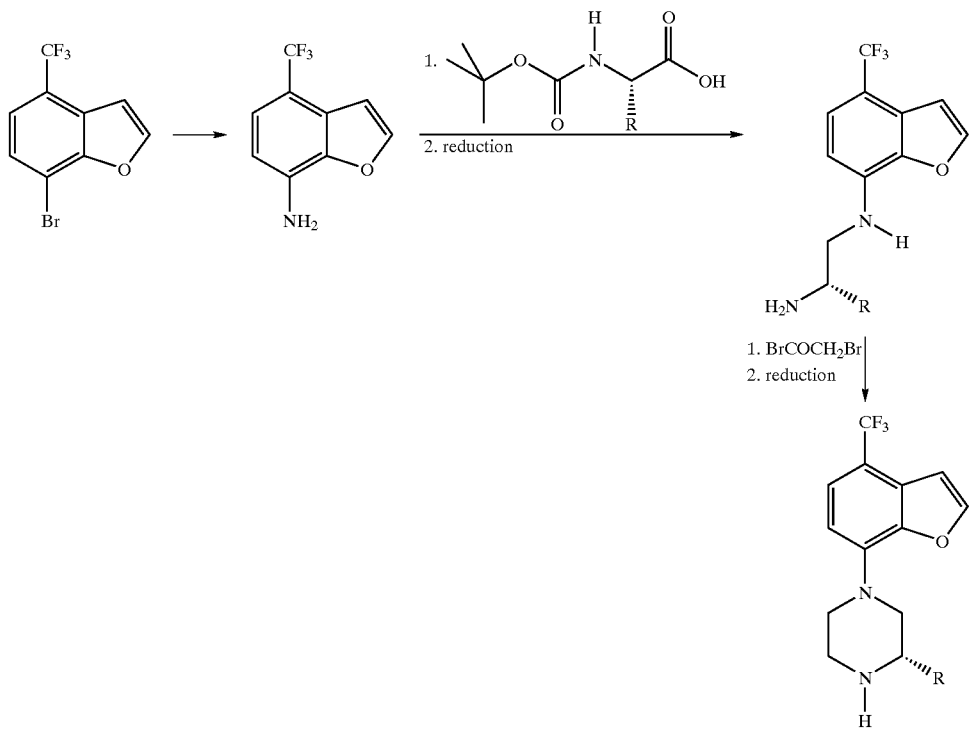

The piperazine ring may be constructed onto the benzofuryl moiety by coupling 4-trifluoromethyl-7-bromobenzofuran with benzophenone imine under the coupling conditions previously described. The resulting adduct is treated with aqueous acid to provide the corresponding amine. This aminobenzofuran is coupled with an appropriately nitrogen-protected (S)-alanine (when R=methyl) or (S)-2-aminobutyric acid (when R=ethyl) under standard peptide coupling conditions. The resulting amide is reduced with a hydride reducing agent such as lithium aluminum hydride, and the corresponding amine deprotected to provide a diamine. The diamine is treated with an appropriate reagent, for example bromoacetyl bromide, to prepare the corresponding lactam. Reduction of this lactam under standard hydride reducing conditions, for example by treatment with borane or lithium aluminum hydride, provide the desired compound.

The requisite benzofuran is either commercially available or may be prepared from an appropriately substituted phenol by methods well known in the art as illustrated in the following scheme.

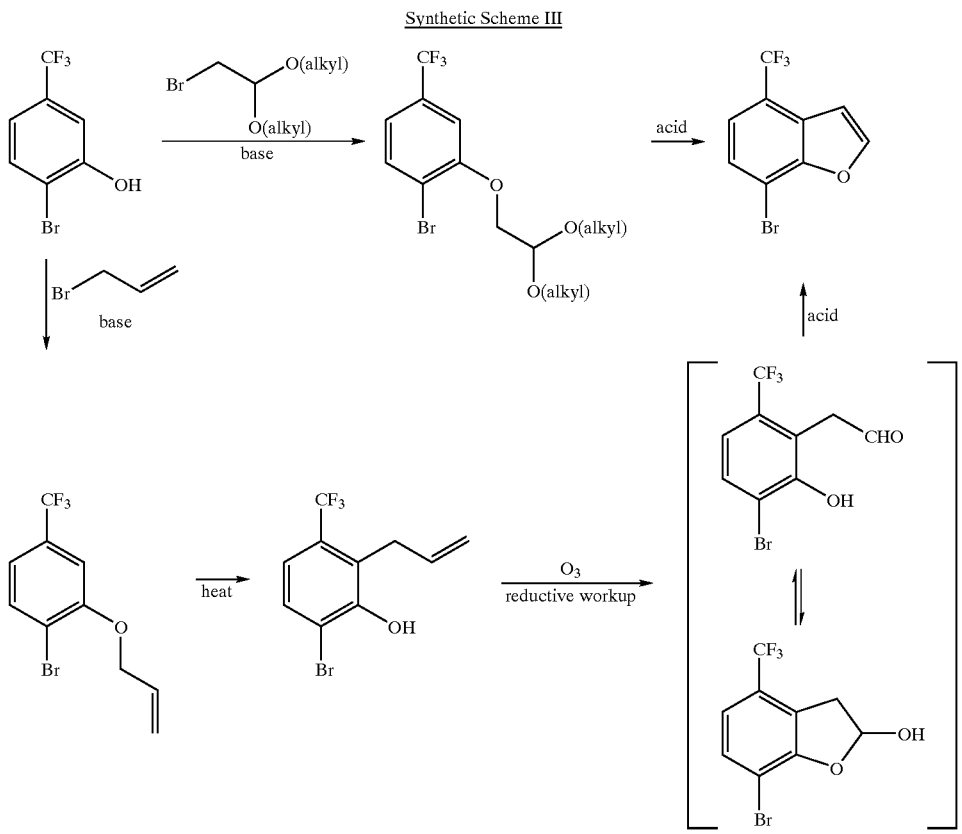

Synthetic Scheme III

A solution of an appropriately substituted phenol in a suitable solvent, typically dimethylformamide, is treated with a base, to generate the corresponding phenoxide. Bases useful for this reaction include hydride sources, such as sodium or potassium hydride, or carbonates, such as sodium or potassium carbonate. The phenoxide solution is then reacted with a chloro- or bromoacetaldehyde protected as a cyclic or dialkyl acetal. Bromoacetaldehyde diethyl acetal is particularly useful for this reaction. The phenoxyacetaldehyde acetal prepared by this procedure is reacted with a source of acid in a suitable solvent to provide the desired benzofuran. Suitable solvents include aromatic solvents such as toluene, xylene, benzene, and halobenzenes such as chlorobenzene. Suitable acids include concentrated sulfuric acid, polyphosphoric acid, and acidic resins such as Amberlyst 15™.

Alternatively, the phenoxide solution is treated with an allyl bromide or allyl chloride to provide, after standard isolation and purification procedures, the corresponding allyl ether. This purified ether is heated at a temperature sufficient to effect an ortho-Claisen rearrangement to provide the corresponding o-allylphenol. It is critical that the allyl ether employed in this rearrangement is substantially free of residual dimethyl-formamide. The o-allylphenol is then treated with an excess of ozone in an appropriate solvent, dichloromethane and methanol are useful solvents for this step. The reaction mixture is then purged of ozone and the ozonide is treated under reducing conditions, typically by treatment with triphenylphosphine or dimethylsulfide, to provide the corresponding phenylacetaldehyde. The skilled artisan will appreciate that the orientation of the aldehyde with the respect to the phenolic hydroxyl group gives rise to the formation of a cyclic hemiacetal. This hemiacetal exists in some equilibrium mixture with the free hydroxyaldehyde. A solution of this equilibrium mixture in a suitable solvent, such as toluene, is treated with a catalytic amount of an appropriate acid, such as sulfuric acid, to provide the desired benzofuran.

The requisite benzofurans may also be prepared from an appropriately substituted phenol as illustrated in the following scheme.

Synthetic Scheme IV

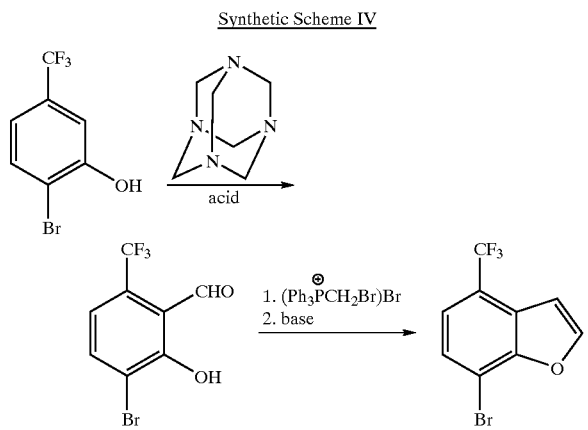

A mixture of an appropriate phenol and hexamethylenetetramine are treated with an appropriate acid, such as trifluoroacetic acid, to provide upon aqueous workup the corresponding o-formylphenol. This o-formylphenol is then treated with (bromomethyl)triphenylphosphonium bromide followed by an appropriate base such as potassium tert-butoxide to provide the desired benzofuran.
R The requisite 2(S)-methylpiperazine is commercially available (Aldrich Chemical Company, Milwaukee, Wis. U.S.A.) Alternatively, both 2(S)-methylpiperazine and 2(S)-ethylpiperazine may be prepared by methods well known in the art (*Org. Prep. Proced. Int.*, 22, 761 (1990)). One such approach is illustrated in the following scheme that illustrates the preparation of 2(S)-methylpiperazine. The skilled artisan will appreciate that 2(S)-ethylpiperazine can also be prepared by the route illustrated in the scheme.

and was then partitioned between 200 mL dichloromethane and 100 mL water. The organic phase was washed with 20 mL saturated aqueous sodium chloride, dried over sodium sulfate and concentrated under reduced pressure. The residue was subjected to silica gel chromatography, eluting with dichloromethane containing 40% hexane. Fractions containing product were combined and concentrated under reduced pressure to provide 48.8 gm (53%) of the desired compound as a yellow oil.

Ion Spray MS: m/e=239, 241 (M+1)

2-bromo-5-trifluoromethyl allyl ether

A mixture of 48.8 gm (0.20 mole) 2-bromo-5-trifluoromethylphenol, 84 gm (0.61 mole) potassium carbonate, and 52.5 mL (0.61 mole) allyl bromide in 2 L acetone was stirred Synthetic Scheme V

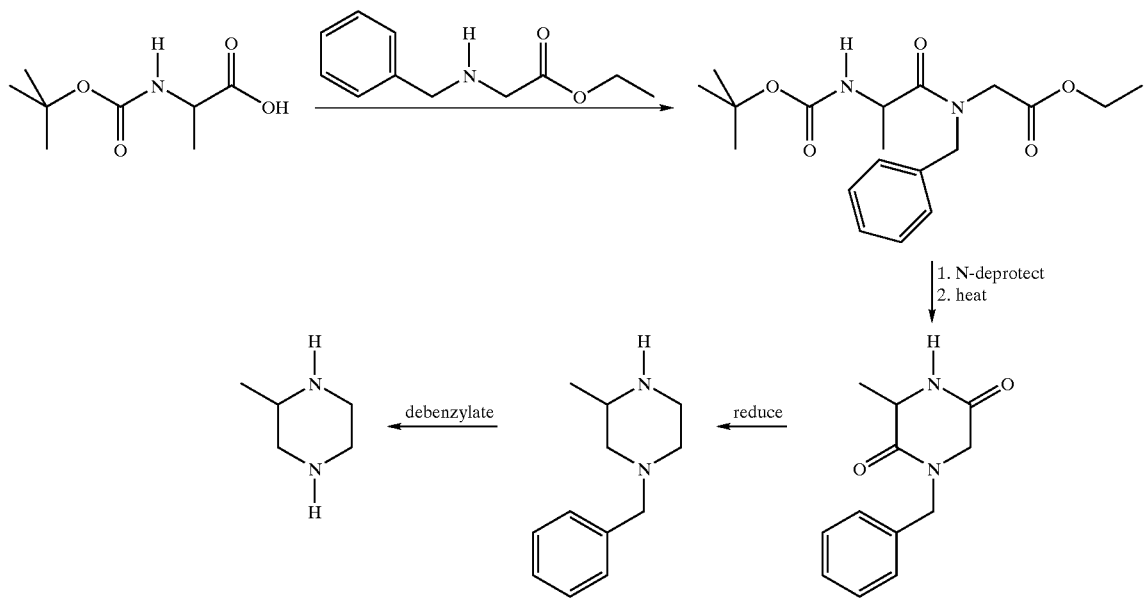

An appropriately N-protected (S)-alanine or (S)-2-aminobutyric acid is coupled with an N-benzylated carboxy-protected amino acid under standard peptide coupling conditions to provide the corresponding dipeptide. This dipeptide is N-deprotected and heated to provide the corresponding dilactam. This dilactam is reduced under standard hydride reducing conditions, for example with lithium aluminum hydride, to provide the corresponding N-benzylated piperazine. The N-benzyl group is removed by either catalytic hydrogenation or by treatment with 1-chloroethyl chloroformate to provide the corresponding piperazine. The benzyl group may be removed either prior or subsequent to coupling with an appropriate benzofuran depending upon the specific coupling orientation desired as described supra.

The following Preparations and Examples are illustrative of methods useful for the synthesis of the compounds of the present invention.

Preparation I 4-trifluoromethyl-7-bromobenzofuran 2-bromo-5-trifluoromethylphenol To a stirred solution of 61.65 gm (0.38 mole) 3-trifluoromethylphenol in 240 mL carbon disulfide were added 19.6 mL (0.38 mole) bromine dropwise. The reaction mixture was stirred at room temperature for about 18 hours at room temperature for about 70 hours. The reaction mixture was filtered and the filtrate concentrated under reduced pressure. The residue was dissolved in 100 mL hexane and this solution was washed sequentially with 2×50 mL water followed by 1×20 mL saturated aqueous sodium chloride. After drying over sodium sulfate, the solution was concentrated under reduced pressure. The residue was subjected to silica gel chromatography, eluting first with hexane and then with 1:1 ethyl acetate:hexane. Fractions containing product were combined and concentrated under reduced pressure to provide 46.2 gm (81%) of the desired compound as a colorless oil.

Claisen Rearrangement

2-Bromo-5-trifluoromethyl allyl ether (43.7 gm, 155 mmol) was heated at 200–212° C. for 3 hours. The reaction mixture was cooled to room temperature and was then subjected to silica gel chromatography, eluting with hexane containing 2.5% ethyl acetate. Fractions containing product were combined and concentrated under reduced pressure to provide 32.4 gm (74%) 2-allyl-3-trifluoromethyl-6-bromophenol as a yellow oil.

Ion Spray MS: 279, 281 (M+1)

Ozonolysis/Dehydration

A solution of 16.2 gm (57.6 mMol) 2-allyl-3-trifluoromethyl-6-bromophenol in 350 mL methanol was cooled to −78° C. Ozone was bubbled into the reaction mixture for about 30 minutes. Nitrogen was then bubbled into the solution to remove excess ozone. To this solution were then added 23 mL dimethyl sulfide and the reaction mixture was stirred at room temperature for about 16 hours. The reaction mixture was concentrated under reduced pressure to provide 21.4 gm of a colorless oil comprising 2-hydroxy-4-trifluoromethyl-7-bromo-1,2-dihydrobenzofuran.

A mixture of this oil in 850 mL chlorobenzene and 48.6 gm Amberlyst 15® which had been dried by azeotropic distillation with chlorobenzene was heated to 70° C. under partial vacuum. The chlorobenzene was slowly removed over 40 minutes. The resulting slurry was washed with 2×250 mL hexane. The hexane washes were combined and concentrated under reduced pressure and the residue was subjected to silica gel chromatography, eluting with hexane. Fractions containing product were combined and concentrated under reduced pressure to provide 8.34 gm (54%) of the title compound as a colorless oil.

$^1$H-NMR(300 MHz, CDCl$_3$): δ 7.81 (d, J=2.0 Hz, 1H); 7.55 (d, J=8.3 Hz, 1H); 7.41 (d, J=8.3 Hz, 1H); 7.03 (m, 1H).

Preparation II 1-tert-butoxycarbonyl-2(S)-ethylpiperazine
2(S)-ethyl-4-benzyl-3,6-dioxopiperazine A mixture of 12.5 gm (61.5 mmol) N-(tert-butoxycarbonyl) 2(S)-aminobutyric acid, 8.3 g (61.4 mmol) 1-hydroxybenzotriazole, 10.7 mL (61.5 mmol) diisopropylethylamine, and 11.8 g. (61.5 mmol) 1-(3-dimethylaminopropyl)-3-ethylcarbodiimide in 150 mL dichloromethane was stirred at 0° C. A solution of 10.8 g (55.9 mmol) N-benzyl glycine ethyl ester in 100 mL dichloromethane was added dropwise to the mixture via addition funnel. The resulting solution was stirred 15 hours at room temperature. The reaction mixture was concentrated under reduced pressure and the residue dissolved in ethyl acetate. This solution was extracted sequentially with 100 mL aliquots of 1N hydrochloric acid, 1N sodium hydroxide, deionized water, and saturated aqueous sodium chloride. The remaining organic phase was dried over MgSO$_4$, filtered, and concentrated under reduced pressure. The resulting residue was dissolved in 100 mL 4N hydrogen chloride in dioxane and stirred for 3 hours at room temperature. The solution was concentrated under reduced pressure and the residue dissolved in 350 mL dichloro-methane. This solution was then treated with 350 mL saturated aqueous sodium bicarbonate. After stirring for 0.5 hours, phases were separated and the organic phase was washed with deionized water, dried over MgSO$_4$, filtered, and concentrated under reduced pressure. The residue resulting residue was crystallized from diethyl ether to afford 8.1 gm (57%) of the desired diketopiperazine.

2(S)-ethyl-4-benzylpiperazine

A solution of 8.1 gm (34.9 mmol) 2(S)-ethyl-4-benzyl-3,6-dioxopiperazine in 50 mL tetrahydrofuran was added dropwise via addition funnel to a solution of 75 mL (75 mMol) lithium aluminum hydride (1M in tetrahydrofuran) and the mixture was heated at reflux for 2.5 h. The reaction was then cooled in an ice bath and was treated sequentially with 3 mL deionized water, 3 mL 5N sodium hydroxide, and 9 mL deionized water. The resulting slurry was allowed to stir for 1 hour and was then filtered. The recovered salts were rinsed with 100 mL tetrahydrofuran and 100 mL dichloromethane. The filtrate was concentrated in vacuo to afford 7.03 g (99%) of the desired piperazine.

Ion Spray MS: m/e=205 (M+H)
Protection/debenzylation

A mixture of 7.03 gm (34.5 mMol) 2(S)-ethyl-4-benzyl-piperazine and 7.8 gm (35.7 mMol) di-tert-butyl dicarbonate in 100 mL dichloromethane was stirred for 1 hour at room temperature. The reaction mixture was concentrated under reduced pressure and 9 gm (29.56 mMol) of the resulting 1-(tert-butoxycarbonyl)-2(S)-ethyl-4-benzylpiperazine were dissolved in 200 mL absolute ethanol. The solution was hydrogenated for 2.5 hour in a Parr shaker at 40 psi over 4.0 gm 10% Pd/C. The slurry was filtered through a celite pad and the filtrate was concentrated under reduced pressure to provide 5.9 gm (94%) of the title compound.

EXAMPLE 1

1-(4-trifluoromethylbenzofur-7-yl)-3(S)-methylpiperazine fumarate 4-trifluoromethyl-7-bromobenzofuran (3.50 g, 13.2 mmol) and 2(S)-methylpiperazine (1.69 g, 16.9 mol) were added to a mixture of racemic 2,2'-bis(diphenylphos-phino)-1,1'-binaphthyl (BINAP) (329 mg, 0.53 mmol, 0.04 eq.), trisdibenzylidene acetone dipalladium (Pd$_2$(dba)$_3$) (242 mg, 0.26 mmol, 0.02 eq.), and sodium t-butoxide (1.78 g, 18.5 mmol, 1.4 eq.) in anhydrous toluene (45 mL) under nitrogen. The reaction mixture was heated at 100° C. for 1.5 h, then allowed to cool to 20° C. and finally poured into diethyl ether (150 mL). The mixure was filtered through celite and the filtrate was concentrated in vacuo. The residue was chromatographed on silica gel using a step gradient of 3% 2M methanolic ammonia in dichloromethane (2 L) and then 4% 2M methanolic ammonia in dichloromethane to afford pure fractions of product (2.02 g, 56%).

Fumaric acid (0.82 g, 1 eq.) was added to a solution of the benzofurylpiperazine (2.02 g) in anhydrous methanol (100 mL). The suspension was sonicated until a clear solution was obtained and the solution was concentrated in vacuo to give a solid. The solid was triturated with diethyl ether and the suspension was stirred for 30 min. The resulting white solid was filtered off and dried under vacuum at 60° C. for 48 h to give the fumarate salt of the title compound (2.73 g, 96%).

[•]$_D$=−21.5° (c=1.0)

$^1$H-NMR (400 MHz, CD$_3$OD): 7.93 (d, J=2.4, 1H, H—C(2)); 7.49 (dd, J=8.3, 1.0, 1H, H—C(5)); 7.0–6.9 (m, 2H, H—C(3) and H—C(6)); 6.68 (s, 2H, vinylic H of fumaric acid); 4.1–4.0 (m, 2H, 2×½ CH$_2$); 3.65–3.55 (m, 1H, CH); 3.54(ddd, J=12.7, 2.4, 2.4, 1H, 0.5 CH$_2$); 3.40 (ddd, J=12.7, 12.7, 3.4, 1H, 0.5 CH$_2$); 3.23, ddd, J=13.7, 10.3, 3.4, 1H, 0.5 CH$_2$); 3.04 (dd, J=13.4, 10.5, 1H, 0.5 CH$_2$); 1. 42 (d, J=6.8, 3H, CH$_3$).

EA: Calculated for C$_{14}$H$_{15}$F$_3$N$_2$O.C$_4$H$_4$O$_4$: C, 54.00; H, 4.78; N, 7.00. Found: C, 53.76; H, 4.62; N, 6.94.

EXAMPLE 2

1-(4-trifluoromethylbenzofur-7-yl)-3(S)-ethylpiperazine fumarate
1-(4-trifluoromethylbenzofur-7-yl)-3(S)-ethyl-4-tert-butoxycarbonylpiperazine Beginning with 1.45 gm (5.47 mMol) 4-trifluoromethyl-7-bromobenzofuran and 1.4 gm (6.53 mMol) 1-(tert-butoxycarbonyl)-2(S)-ethylpiperazine, 1.82 gm (84%) of the desired compound were prepared essentially as described in Example 1.

ESMS: m/e=399 (M+1)
Deprotection

A solution of the 1-(tert-butoxycarbonyl)-2(S)-ethylpiperazine prepared above in 20 mL dichloromethane was cooled in an ice bath and treated with 20 mL trifluoroacetic acid and the reaction mixture was allowed to stir for 5 hours at room temperature. The organics were concentrated under reduced pressure and the residue was dissolved in 200 mL ethyl acetate. This solution was extracted sequentially with saturated aqueous sodium bicarbonate (3×100 mL), deionized water (100 mL), and saturated aqueous sodium chloride (100 mL). The organic phase was dried over magnesium sulfate, filtered, and the filtrate was concentrated under reduced pressure to provide 1.24 gm (91%) of 1-(4-trifluoromethylbenzofur-7-yl)-3(S)-ethylpiperazine.

ESMS: m/e=299 (M+1)

This piperazine was dissolved in 20 mL absolute ethanol and the solution was filtered. The filtrate was heated to reflux and treated with 0.48 gm fumaric acid. The mixture was heated for five minutes until all the solids dissolved. The solution was concentrated under reduced pressure and the residue was triturated with 50 mL diethyl ether. The slurry was allowed to stir for 0.5 hour, was filtered, and the white solid was rinsed with 2×20 mL diethyl ether. The solid was dried at 60° C. under reduced pressure for 4 hours to provide 1.39 g (81%) of the title compound.

mp=163–164.5° C.

EA: Calculated for $C_{15}H_{17}F_3N_2O \cdot C_4H_4O_4$: C, 55.07; H, 5.11; N, 6.76. Found: C, 54.98; H, 5.09; N, 6.77.

$[\alpha]_D^{20}$ (Methanol, c=10.2 mg/mL)=−9.81°

The ability of the compounds of Formula I to bind to the 5-$HT_{2c}$ receptor subtype was measured essentially as described by Wainscott (Wainscott, et al., *Journal of Pharmacology and Experimental Therapeutics*, 276, 720–727 (1996)).

Membrane Preparation

AV12 cells stably transfected with the human 5-$HT_{2c}$ receptors were grown in suspension and harvested by centrifugation, resuspended in 50 mM tris-HCl, pH 7.4, and frozen at −70° C. On the day of assay, an aliquot of cells was thawed, resuspended in 40 mL of 50 mM tris-HCl, pH 7.4, and centrifuged at 39,800×g for 10 minutes at 4° C. The resulting pellet was resuspended, incubated at 37° C. for 10 minutes to remove endogenous serotonin, then centrifuged twice more.

$[^{125}I]$-DOI Binding for Determination of 5-$HT_{2c}$ Receptor Affinity

Briefly, prepared cell membranes were added to dilutions of compounds in a final solution containing 50 mM tris-HCl, pH 7.4, 9.75 mM $MgCl_2$, 0.5 mM EDTA, 10 μM pargyline, 0.1% sodium ascorbate, and 0.1 nM $[^{125}I]$-DOI, with 10 μM mianserin for defining non-specific binding. All incubations (800 μL) were performed at 37° C. for 30 minutes before harvesting onto GF/C filters prewet with 0.5% polyethyleneimine, with four 1 mL washes of ice-cold 50 mM tris-HCl, pH 7.4, and counting in a gamma counter. Nonlinear regression analysis was performed on the concentration response curves using a four parameter logistic equation described by DeLean (DeLean, et al., *Molecular Pharmacology*, 21, 5–16 (1982)). $IC_{50}$ values were converted to $K_i$ values using the Cheng-Prusoff equation (Cheng, et al., *Biochem. Pharmacol.*, 22, 3099–3108 (1973)).

The compounds of EXAMPLES 1 and 2 were tested in this assay and were found to have affinity for the 5-$HT_{2c}$ receptor. The selectivity of these compounds for the 5-$HT_{2c}$ receptor relative to other serotonergic receptors is demonstrated by the data in the following table.

| 5-HT RECEPTOR | Compound of Example 1 $K_i$ (nM) | Compound of Example 2 $K_i$ (nM) |
| --- | --- | --- |
| 1a | 134.35 | 261 |
| 1b | 260.30 | 2937 |
| 1d | 147.25 | 726 |
| 1e | 632.60 | 1143 |
| 1f | 162.75 | 1000 |
| 2a | 37.65 | 27.76 |
| 2b | 176.85 | 177.03 |
| 2c | 2.41 | 0.77 |
| 4 | 977.30 | NOT DETERMINED |
| 6 | 225.05 | 607 |

The 5-$HT_{2C}$ receptor is functionally coupled to specific G-proteins. Agonist activation of 5-$HT_{2C}$ G-protein-coupled receptors results in the release of GDP from the •-subunit (G alpha q or G alpha i) of the G-protein and the subsequent binding of GTP. The binding of the stable analog $[^{35}S]$-GTPγS is an indicator of this receptor's activation.

$[^{35}S]$-GTPγS Binding

The immunoadsorption scintillation proximity assay (ISPA) in microtiter plates of $[^{35}S]$-GTPγS binding to G alpha q or G alpha i was modified from published conditions (DeLapp et al, JPET 289 (1999) 946–955). Test compounds were dissolved in DMSO and diluted in assay buffer consisting of 50 mM Tris-HCl (pH 7.4), 10 mM $MgCl_2$, 100 mM NaCl, and 0.2 mM EGTA. Incubations were performed over 12 test concentrations; volume was 200 μl. The incubation also contained 0.1 μl GDP and 0.25 nM $[^{35}S]$-GTPγS. Membrane homogenates from AV12 cells stably transfected with the human 5-$HT_{2C}$ receptor were added and the microtiter plates were incubated for 30 minutes at room temperature. The incubation was terminated by the addition of Nonidet P-40 (final concentration of 0.27%), followed by addition of rabbit polyclonal anti-G alpha q/11 antibody (0.2 μg per well), and anti-rabbit scintillation proximity assay beads (Amersham; 1.25 mg per well; final volume was 290 μl). The mixture was incubated for 3 hours at room temperature to complete the immunoadsorption of $[^{35}S]$-GTPγS bound to G alpha q/11. Microtiter plates were centrifuged briefly to pellet beads. $[^{35}S]$-GTPγS binding was quantitated by microtiter plate scintillation spectrometry (Wallac). Data analysis was performed by nonlinear regression analysis with GraphPad Prism software running on a personal computer, using 5-HT control concentration-response curves to define maximal stimulation of $[^{35}S]$-GTPγS binding.

1-(4-trifluoromethylbenzofur-7-yl)-3(S)-methylpiperazine fumarate was tested in the $[^{35}S]$-GTPγS assay and was found to be an agonist of the 5-$HT_{2c}$ receptor, $EC_{50}$ =8.5 nM. 1-(4-trifluoromethylbenzofur-7-yl)-3(S)-ethylpiperazine fumarate was tested in the $[^{35}S]$-GTPγS assay and was also found to be an agonist of the 5-$HT_{2c}$ receptor, $EC_{50}$ =7.8 nM.

The ability of agonists of the 5-$HT_{2c}$ receptor in general to treat obesity is demonstrated by testing in a feeding assay.

Fasted Feeding Assay

Male rats are fasted for 18 hours prior to testing. Rats are first assigned to either a treatment or control group (N=8), then weighed, administered drug or vehicle orally, and returned to their home cage. Thirty minutes later, food is made available to the animals. The food and the food hopper are weighed before, one hour, two hours, and four hours after food is made available to the test animals. Weight of food consumed plus spillage by the treatment animals is compared to food consumed plus spillage by control animals using a one-way ANOVA, with a Dunnett's. post-hoc test.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., Remington's Pharmaceutical Sciences, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
| --- | --- |
| Compound of EXAMPLE 1 | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Compound of EXAMPLE 2 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Compound of EXAMPLE 1 | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Compound of EXAMPLE 2 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Compound of EXAMPLE 1 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Compound of EXAMPLE 2 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
| --- | --- |
| Compound of EXAMPLE 1 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
| --- | --- |
| Compound of EXAMPLE 2 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
| --- | --- |
| Compound of EXAMPLE 1 | 250.0 mg |
| Isotonic saline | 1000 ml |

FORMULATION EXAMPLE 10

A topical formulation may be prepared as follows:

| Ingredient | Quantity |
| --- | --- |
| Compound of EXAMPLE 2 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
|---|---|
| Compound of EXAMPLE 1 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:
1. A compound of formula

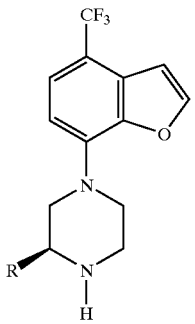

where R is methyl or ethyl, or a pharmaceutically acceptable acid addition salt thereof.

2. A compound of claim 1 where R is methyl.
3. A compound of claim 1 where R is ethyl.
4. A pharmaceutical formulation which comprises, in association with a pharmaceutically acceptable carrier, diluent or excipient, a compound of Formula I:

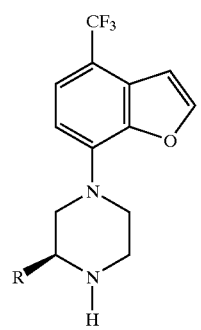

where R is methyl or ethyl, or a pharmaceutically acceptable acid addition salt thereof.

5. A pharmaceutical formulation of claim 4 where R is methyl.
6. A pharmaceutical formulation of claim 4 where R is ethyl.
7. A method for the treatment of obesity in mammals, comprising administering to mammal in need of such treatment an effective amount of a compound of Formula I:

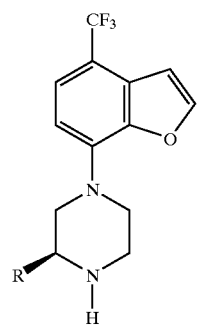

where R is methyl or ethyl, or a pharmaceutically acceptable acid addition salt thereof.

8. The method of claim 7 where the mammal is human.
9. The method of claim 8 where R is methyl.

10. The method of claim 8 where R is ethyl.

11. A method for the treatment of obsessive compulsive disorder in mammals, comprising administering to a mammal in need of such treatment a pharmaceutically effective amount of a compound of Formula I:

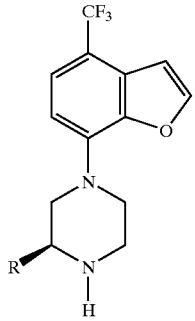

where R is methyl or ethyl, or a pharmaceutically acceptable acid addition salt thereof.

12. The method of claim 11 where the mammal is human.
13. The method of claim 12 where R is methyl.
14. The method of claim 12 where R is ethyl.

15. A method for the treatment of depression in mammals, comprising administering to a mammal in need of such treatment a pharmaceutically effective amount of a compound of Formula I:

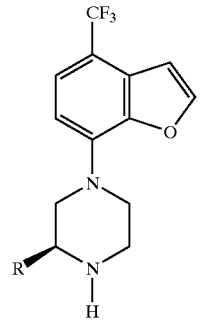

where R is methyl or ethyl, or a pharmaceutically acceptable acid addition salt thereof.

16. The method of claim 15 where the mammal is human.
17. The method of claim 16 where R is methyl.
18. The method of claim 16 where R is ethyl.

* * * * *